United States Patent [19]
Nakaso et al.

[11] Patent Number: 5,402,681
[45] Date of Patent: Apr. 4, 1995

[54] ULTRASONIC MICRO SPECTROMETER

[75] Inventors: Noritaka Nakaso, Kasukabe; Yusuke Tsukahara, Tokyo; Masao Saito, Tokyo; Katsumi Ohira, Ageo, all of Japan

[73] Assignee: Toppan Printing Co., Ltd., Tokyo, Japan

[21] Appl. No.: 267,767

[22] Filed: Jul. 5, 1994

Related U.S. Application Data

[63] Continuation of Ser. No. 773,829, Oct. 9, 1991, abandoned.

[30] Foreign Application Priority Data

Nov. 28, 1990 [JP] Japan .................................. 2-328180

[51] Int. Cl.6 ............................................. G01N 29/10
[52] U.S. Cl. ........................................ 73/602; 73/606; 73/624
[58] Field of Search ................ 73/602, 606, 607, 620, 73/624

[56] References Cited

U.S. PATENT DOCUMENTS

| | | | |
|---|---|---|---|
| 3,978,714 | 9/1976 | Shraiber et al. | |
| 3,996,791 | 12/1976 | Niklas et al. | 73/602 |
| 4,098,129 | 7/1978 | Deblaere et al. | 73/602 |
| 4,625,556 | 12/1986 | Sukahara et al. | 73/602 |
| 5,038,787 | 8/1991 | Antich et al. | 73/602 |
| 5,079,952 | 1/1992 | Nakaso et al. | 73/624 |

FOREIGN PATENT DOCUMENTS 2412842 7/1979 France .

OTHER PUBLICATIONS

"Local Critical Angle Measurement for the Examination of Materials", by G. L. Fitzpatrick, B. P. Hildebrand, and A. J. Boland, 1983 Ultrasonics Symposium, pp. 899–904.

Ultrasonics International 89 Conference Proceedings "Measurements of the Layer Thickness and Adhesion with High Spatial Resolution by an Ultrasonic Micro Spectrometer", N. Nakaso et al.

Proceedings of 10th Symposium on Ultrasonic Electronics, Tokyo 1989, Japanese Journal of Applied Physics, vol. 29 (1990) Supplements 29–1, pp. 289–291 "Measurements of SAW Velocity Using an Ultrasonic-Micro Spectrometer" K. Ohira et al.

1990 Ultrasonics Symposium, "An Ultrasonic Micro-Spectrometer for the Evaluation of Elastic Properties with Microscopic Resolution" Y. Tsukahara et al.

*Primary Examiner*—John E. Chapman
*Attorney, Agent, or Firm*—Armstrong, Westerman, Hattori, McLeland & Naughton

[57] ABSTRACT

An ultrasonic sensor for use in an ultrasonic micro spectrometer includes a concave surface transducer having a concave ultrasonic wave transmitting/receiving surface and a plane transducer having a plane transmitting/receiving surface. The concave surface transducer is capable of transmitting converging ultrasonic waves toward a specimen, wherein the waves are reflected from the surface of the specimen and are received by the plane transducer which outputs electric signals corresponding to the intensity of the reflected ultrasonic waves. Based on a signal output from the ultrasonic sensor, a digital oscilloscope and FFT analyzer forms a distribution of spectral intensity indicating the intensity of the reflected wave as a function of frequency. The digital oscilloscope and FFT analyzer further forms a distribution of spectral phase indicating the spectral phase of the reflected waves as a function of frequency. Either the distribution of spectral intensity or of spectral phase can effectively be analyzed for evaluating elastic characteristics and structure of a specimen.

19 Claims, 14 Drawing Sheets

ULTRASONIC MICRO SPECTROMETER

This application is a continuation of application Ser. No. 07/773,829, filed Oct. 9, 1991, now abandoned.

BACKGROUND OF THE INVENTION

1. Field of the Invention

The present invention relates to an ultrasonic micro spectrometer for measuring and evaluating physical characteristics of a sample, measuring thickness of layers of laminated samples, and judging adhesion between layers of a sample, for example.

2. Description of the Related Art

The present inventors have previously disclosed an ultrasonic micro spectrometer in their earlier application, U.S. Ser. No. 07/495,961 (now U.S. Pat. No. 5,079,952) which incorporates a sensor composed of ultrasonic transducers making up transmitters and receivers in pairs capable of independently executing transmission and reception of ultrasonic waves. One of the ultrasonic transducers in the pair contains a recessed or concave transmission/reception surface, whereas the other ultrasonic transducer contains a planar transmission/reception surface. Either of the above-mentioned transducers may be provided for receiving or for transmitting waves. For explanatory purposes, an example of the operation of the above ultrasonic micro spectrometer is described below, wherein one of the ultrasonic transducers having a concave surface serves as a transmitter and the ultrasonic transducer having a planar surface serves as a receiver for example.

When the transmitter receives a wide-band high frequency voltage pulse, wide-band high-frequency ultrasonic waves are generated from the concave surface of the ultrasonic transducer. The wide-band high-frequency ultrasonic waves are transmitted onto the surface of a sample while being converged by the concave surface of the transmitter. Upon arrival at the surface of the sample, the converged ultrasonic waves scatter in a direction corresponding to an aperture angle of the concave surface of the transmitter before being reflected by the surface of the sample. The reflected waves are received by the planar receptive surface of the other ultrasonic transducer, serving as a receiver, in a wide variety of directions. The received waves are converted into electric signals corresponding to the intensity of the reflected waves before being delivered to a spectroanalyzer.

Next, based on the signal output from the receiver, the spectroanalyzer forms a distribution of the spectral intensity indicating the intensity of the reflected waves as a function of frequency. Response characteristics of a variety of frequency components can be analyzed by referring to the distribution of the spectral intensity. Based on the results of the analysis of response characteristics, the ultrasonic micro spectrometer evaluates the physical characteristics of the sample and measures the thickness of laminated layers of the sample.

When the reflected waves are converted into electric signals by the receiver, since the receiver has a planar receptive surface, those reflective waves containing components capable of orthogonally intersecting the planar surface are effectively converted into electric signals. On the other hand, those reflective waves containing other, non-orthogonal components cannot fully be converted into electric signals. Because of this, the reflective waves which are converted by the receiver are extremely dependent on the physical characteristics of the sample when receiving ultrasonic waves at a specific angle of incidence.

As a result, when scanning the transmitted waves along the surface of the objective sample, variation of the spectral intensity of the reflected waves can precisely be detected in each measuring position. The spectral intensity is further varied based on the elastic characteristics and surface condition of the sample.

Nevertheless, when dealing with a sample containing certain characteristics which may prevent the intensity of reflected waves from being dependent on the frequency or the angle of incidence of the ultrasonic waves, no variation occurs at all in the intensity of the reflected waves, and hence a useful analysis cannot be obtained. As a result, no concrete data on the sample can be generated. This in turn indicates that conventional ultrasonic micro spectrometers are subject to limitations in that the range of possible samples available for evaluation is restricted.

SUMMARY OF THE INVENTION

Therefore, an object of the invention is to fully solve the above problems by providing a novel ultrasonic micro spectrometer which is capable of securing measurement of elastic constants and elastic characteristics of such a sample containing specific characteristics which would prevent the intensity of reflected waves from being dependent on frequency or angle of incidence of the ultrasonic waves, and yet, which is capable of correctly measuring the thickness and judging adhesion between laminated layers of the sample.

The invention provides a novel ultrasonic micro spectrometer for executing ultrasonic spectroscopy, which initially transmits ultrasonic waves to a sample, and then receives reflected ultrasonic waves before eventually analyzing frequencies. Characteristically, the ultrasonic micro spectrometer embodied by the invention includes the following:

means for generating high-frequency signals;

an ultrasonic transducer assembly incorporating first and second ultrasonic transducer units; wherein the first ultrasonic transducer unit contains a piezoelectric film inserted between a pair of electrodes and a concave ultrasonic transmission/reception surface which allows transmission of converged waves or reception of reflected ultrasonic waves; wherein the second ultrasonic transducer unit contains a plane piezoelectric film inserted between a pair of plane electrodes and a plane transmission/reception surface which allows transmission of plane waves or reception of reflected ultrasonic waves; wherein upon receipt of high-frequency signals output from the high-frequency generator, either of the first and second ultrasonic transducer units transmits ultrasonic waves to the sample; and wherein the other ultrasonic transducer unit receives ultrasonic waves reflected from the sample, and then outputs electric signals corresponding to the intensity of the reflected waves;

a table for mounting the sample thereon;

scanning means for moving at least one of the ultrasonic transducer assembly and the sample mounted on the table relative to one another in order that a focal position of the ultrasonic waves transmitted from one of the ultrasonic transducer units is scanned two-dimensionally along a surface of the sample, wherein the focal position of the transmitted ultrasonic waves is determined by the shape of the ultrasonic transmission surface of the ultrasonic transducer unit which receives the high-frequency signals;

means for controlling an angle of incidence and a reflective angle of the ultrasonic transducer assembly by inclining at least the second ultrasonic transducer unit in a direction for varying the angle of incidence and the reflective angle, wherein the angle of incidence and the reflective angle are respectively prescribed to be a specific angle formed by the normal of the plane of the second ultrasonic transducer unit and the normal of the surface of the objective sample;

means for forming a distribution of spectral intensity indicating the intensity of reflected waves in the form of a function of frequency based on signals output from the ultrasonic transducer assembly; and means for forming a distribution of phase spectrum indicating the phase of the reflected waves in the form of a function of frequency based on the distribution of the spectral intensity.

Note that the ultrasonic micro spectrometer according to the present invention is hereinafter called "USMS" by way of abbreviation.

According to the invention, the angle of incidence and the reflective angle in relation to the ultrasonic transducer assembly are respectively variable under operation of an incident angle/reflective angle control unit.

Whenever ultrasonic waves are transmitted onto the surface of the sample at a specific angle of incidence which is dependent on the elasticity of the sample and the elasticity of a liquid coupler, elastic surface waves are excited on the surface of the sample. As the elastic surface waves propagate along the direction of the surface of the sample, the intensity of the reflective waves declines. When measuring the intensity of the reflective waves, the phase of the reflective waves also varies at a specific angle of incidence. Such a variation in phase can be detected by referring to the distribution of the phase spectrum. Based on the distribution of the phase spectrum, the ultrasonic micro spectrometer according to the present invention can correctly measure elastic constants and elastic characteristics of a sample, notwithstanding the fact that such a sample may not exhibit any effect with respect to the intensity of the reflected waves being dependent on the frequency or the angle of incidence of ultrasonic waves. As a result, the ultrasonic micro spectrometer can correctly measure the thickness of laminated layers and judge the adhesion of laminated layers of the sample, even with samples which would not allow such measurements on the basis of reflected wave intensity.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 21 and 22 graphically designate the relationship between the angle of incidence and the intensity of ultrasonic waves and the relationship between the angle of incidence and phase characteristics, when the intensity of the reflected ultrasonic waves is not dependent on the angle of incidence;

FIG. 23 graphically designates the relationship between the angle of incidence and frequency characteristics when variation of phase occurs;

DETAILED DESCRIPTION OF THE PREFERRED EMBODIMENTS

Figure 1:
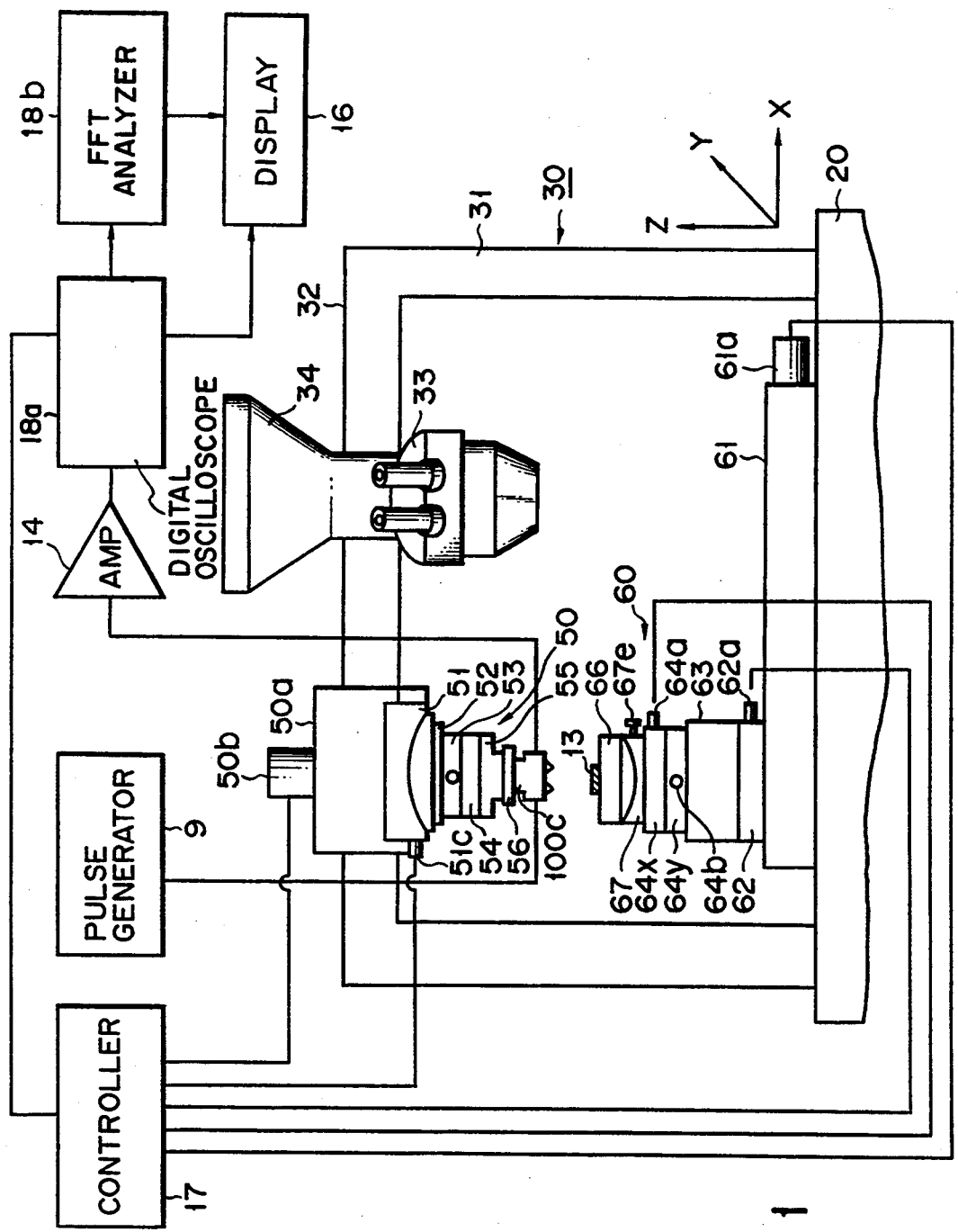
FIG. 1 schematically illustrates an overall block diagram of an ultrasonic micro spectrometer (USMS) according to the first embodiment of the invention.
Figure 2:
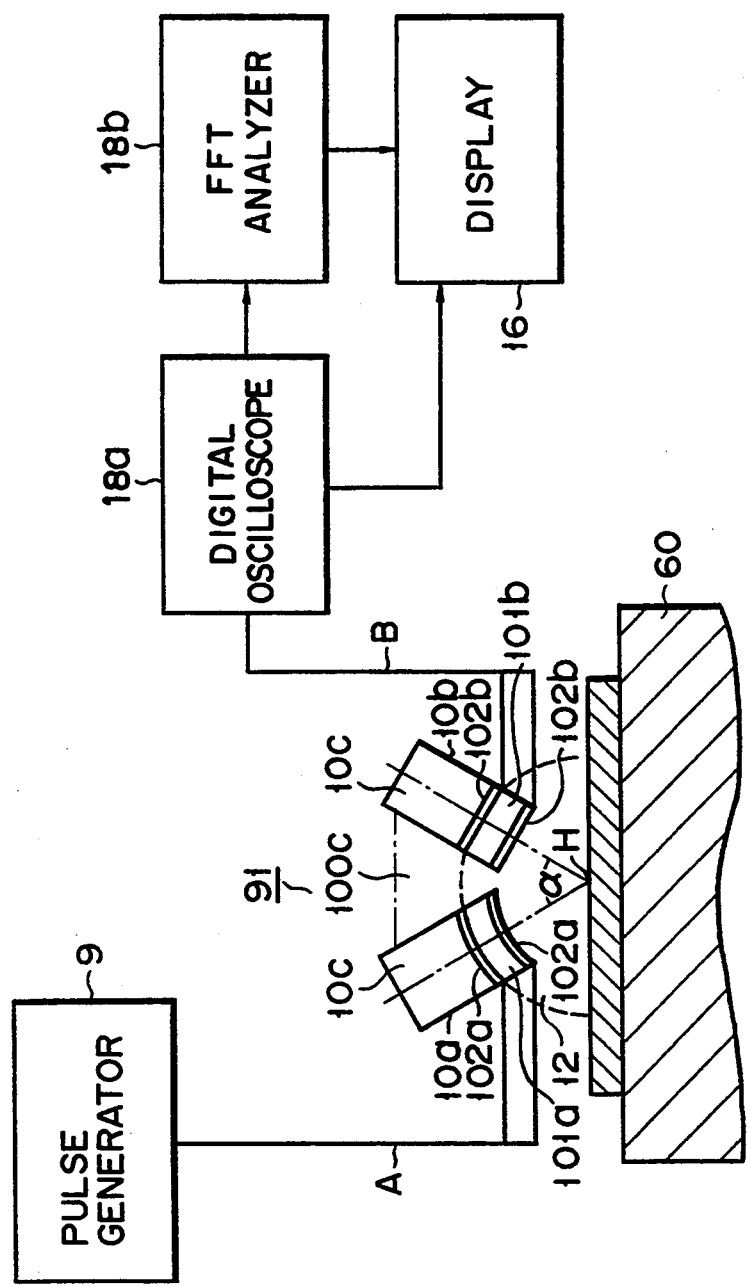
FIG. 2 schematically illustrates an overall block diagram of an ultrasonic micro spectrometer (USMS) according to the first embodiment of the invention.

FIG. 1 schematically illustrates an overall block diagram of an ultrasonic micro spectrometer ("USMS") according to the first embodiment of the invention. FIG. 2 illustrates a schematic arrangement of the ultrasonic micro spectrometer shown in FIG. 1.

As shown in FIG. 2, ultrasonic sensor 91 independently executes transmission and reception of ultrasonic waves, and is characteristically composed of the following: a pair of ultrasonic transducers comprising a concave-surface transducer 10a which is provided with a concave ultrasonic transmission or reception surface and a plane transducer 10b provided with a plane ultrasonic transmission or reception surface. The concave transducer 10a and the plane transducer 10b may each be employed as either an ultrasonic transmitter or an ultrasonic receiver, respectively. The focal position of the ultrasonic sensor 91 is determined by the design of the transmission/reception surfaces. More specifically the concave-surface transducer 10a is composed of a curved piezoelectric film 101a made from zinc oxide film, for example, and a pair of curved electrode sheets 102a made from gold film sandwiching the curved piezoelectric film 101a. The plane transducer 10b is composed of a plane piezoelectric film 101b made from zinc oxide film, for example, and a pair of plane electrode sheets 102b made from gold film sandwiching the plane piezoelectric film 101b. The piezoelectric films 101a and 101b respectively have a diameter of several millimeters and a thickness of about 10 microns. The curved electrode sheets 102a and the plane electrode sheets 102b respectively have a diameter of about 2 millimeters.

The concave-surface transducer 10a and the plane transducer 10b are respectively held by cylindrical holders 10c. Each of these cylindrical holders 10c has a diameter of about 10 millimeters and a length of several centimeters. The concave-surface transducer 10a and the plane transducer 10b are respectively manufactured by sequentially laminating the component films on a holder 10c made from resin by applying either vacuum evaporation or a sputtering process. The component films include a gold film 102a (102b), a zinc oxide film 101a (101b), and an additional gold film 102a (102b).

Each of the holders 10c is secured inside a case 100c (described later on) in order that a constant angle $\alpha$ can be maintained between the center line of the concave transmission/reception surface of the concave-surface transducer 10a and the center line of the plane transmission/reception surface of the plane transducer 10b, as shown in FIG. 2. A liquid coupler 12, substantially consisting of water, is stored between a sample 13 mounted on a multiple-stage table 70 and the ultrasonic sensor 91.

A pulse generator 9 generates a predetermined high-frequency voltage signal containing a specific frequency selected from high-frequency bands ranging from 10 through 1,000 MHz. For example, a burst signal generated while sweeping across a predetermined frequency range may be employed for the high-frequency voltage signal. The burst signal is delivered to the concave-surface transducer 10a of the ultrasonic sensor for example. Upon receiving the burst signal, the concave surface transducer 10a transmits convergent-monowavelength waves into the liquid coupler 12 from the concave ultrasonic transmission/reception surface. In this case, if the concave-surface transducer 10a has a concave recessed surface, then, the transmitted waves are converged into a point, whereas if the concave-surface transducer 10a has a cylindrical concave surface, then the transmitted waves are linearly converged. At the same time, the transmitted waves are reflected by the surface of the sample 13, and then, the reflected waves again propagate through the liquid coupler 12 before being received by the plane transducer 10b. The plane transducer 10b converts the received reflected waves into electric signals, and then outputs these electric signals to an amplifier 14. The electric signals amplified by the amplifier 14 are then delivered to a digital oscilloscope 18a. The digital oscilloscope 18a is used for detecting time-based waveforms from the signals output from the ultrasonic sensor 92. A fast Fourier transformation (FFT) analyzer 18b transforms the detected time-based waveforms into a Fourier series at a fast speed, and simultaneously forms the distribution of spectral intensity and the distribution of spectral phase. The operating system of the present invention, comprising a controller 17, consecutively performs the above-mentioned measuring processes while sweeping the frequency of the burst signals supplied to the transducer 10a. This eventually results in the formation of a distribution of spectral intensity, designating the intensity of the reflected waves as a function of frequency. In addition, a distribution is generated of the phase of the spectrum, designating the phase of the reflected waves as a function of frequency. The distribution of the spectral intensity and the distribution of the spectral phase are respectively shown on a display screen 16.

Figure 3:
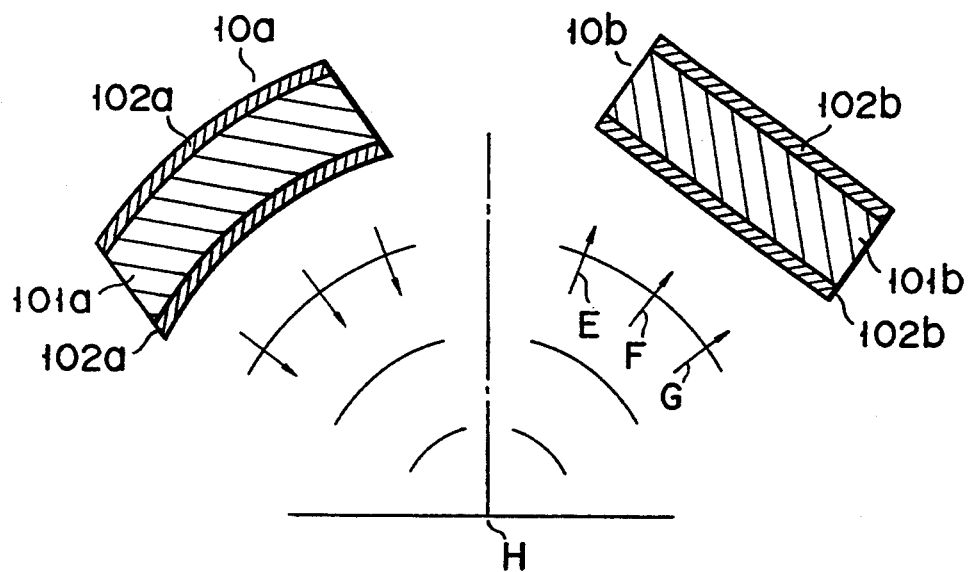
FIG. 3 through 5 respectively illustrate sectional views explaining the functional operation of the ultrasonic micro spectrometer shown in FIG. 1, wherein a concave-surface transducer is employed for transmission and a plane transducer is employed for reception of ultrasonic waves.
Figures 4, 5:
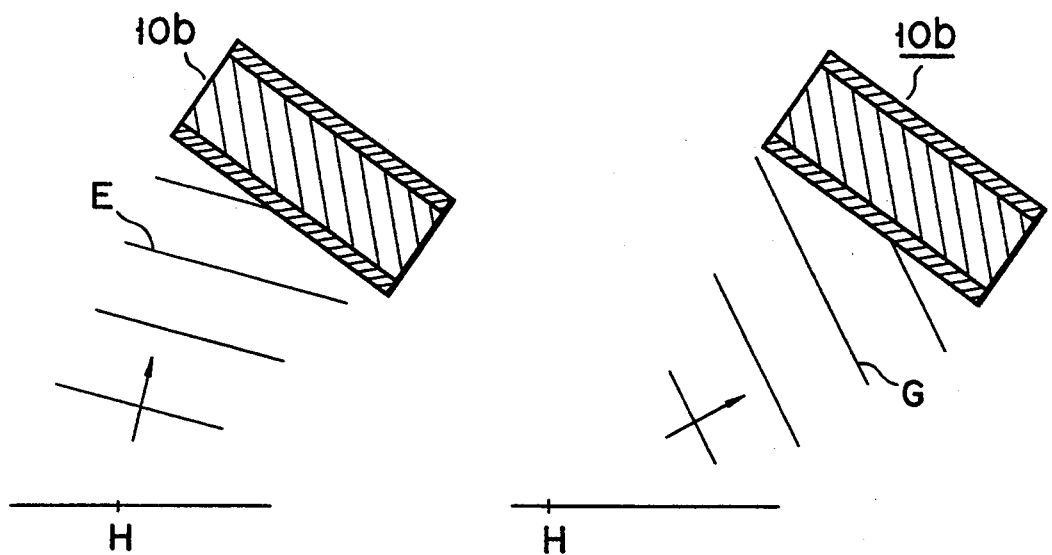

As shown in FIG. 3, when the concave-surface transducer 10a is employed for transmission and the plane transducer 10b is employed for reception, ultrasonic waves are transmitted from the concave surface of the concave-surface transducer 10a in the direction shown by the arrows, so that the transmitted ultrasonic waves have a curved wavefront. Likewise, the plane surface transducer 10b receives ultrasonic waves having a curved wavefront. The plane surface transducer 10b further receives ultrasonic waves reflected from a single point H. Nevertheless, as is clear from FIGS. 3 through 5, ultrasonic waves reflected from the point H, although generally having a curved wave front, actually consist of a plurality of combined plane-wave components E, F, and G containing a variety of wave fronts oriented in different directions. As is clear from FIGS. 4 and 5, those wave components E and G cannot effectively be converted into electric signals because of phasewise interference generated on the surface of the piezoelectric film 102b. Accordingly, among the variety of ultrasonic waves reflected at the point H, only those specific reflective waves having wavefronts designated by the component F can reliably be received by the plane transducer 10b with any substantial effect. In other words, this in turn indicates that the ultrasonic sensor 91 only outputs signals corresponding exactly to those components reflected at a specific angle defined between the plane transducer 10b and the sample 13. When the plane transducer 10b is employed for reception of ultrasonic waves, the angle of incidence must correspond to the reflective angle, and in addition, even when the plane transducer 10b is employed for transmission, the angle of incidence also must correspond to the reflective angle.

As mentioned earlier, signals output from the ultrasonic sensor 91 contain substantial intensity, and in addition, these signals reflect the physical characteristics, in particular elastic characteristics, of the sample material present at the point H. Therefore, when operating the ultrasonic sensor 91, ultrasonic waves transmitted from the concave transducer 10a are converged to a point H which substantially corresponds to the focal point of the concave transducer 10a. As a result, extremely high spatial resolution can be achieved. On the other hand, when the ultrasonic sensor 91 transmits and receives signals, it is essential that the angle of incidence be set within a predetermined range of angles with extreme precision. Such precision can reliably be achieved by employing the Θ-axial goniometer 51 of the sensor driving mechanism 50, to be described later on. Owing to this arrangement, the plane transducer 10b effectively receives only those ultrasonic waves which are reflected at a desired reflective angle, thus permitting the system to maintain constant reliability.

Figure 6:
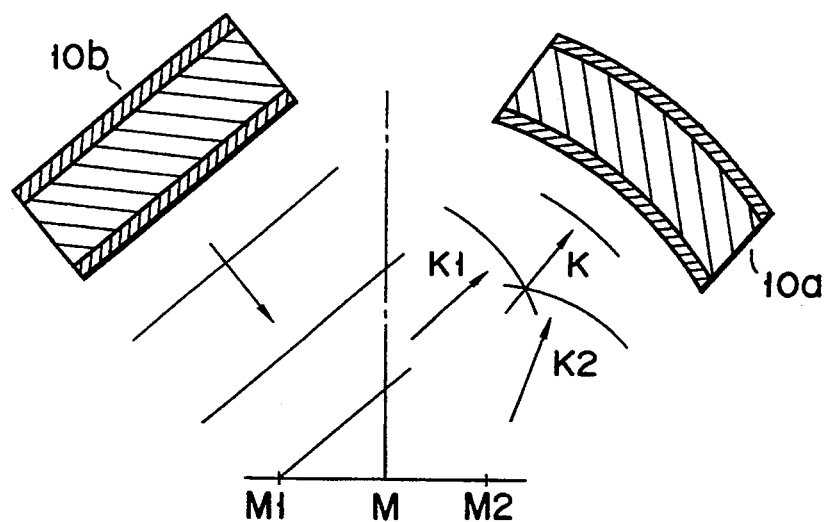
FIGS. 6 through 9 respectively illustrate sectional views explaining the functional operation of the ultrasonic micro spectrometer shown in FIG. 1, wherein a plane transducer is employed for transmission and a concave-surface transducer is employed for reception of ultrasonic waves.
Figure 7:
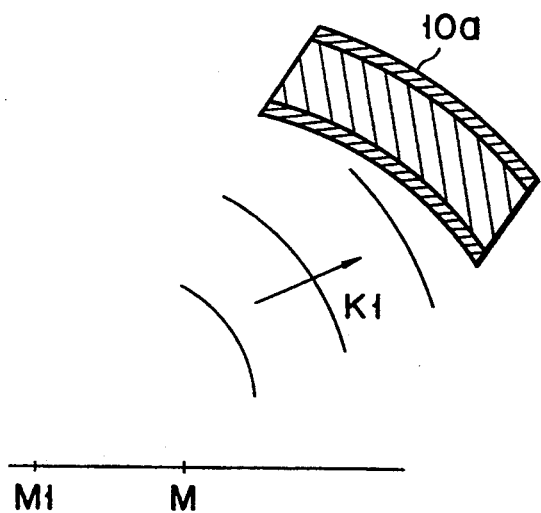
Figure 8:
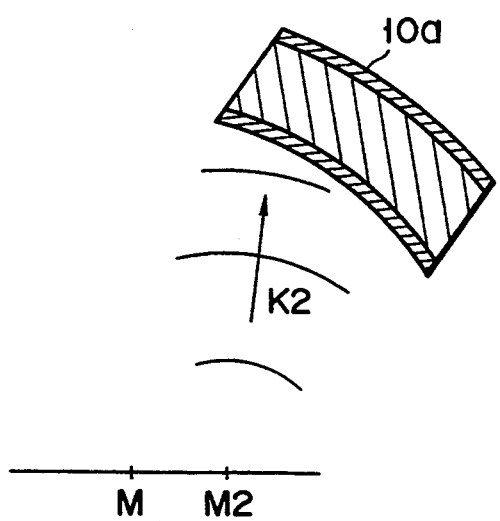

As is clear from the following description in reference to FIGS. 6 through 8, even when the plane transducer 10b is used for the transmission of ultrasonic waves and the concave-surface transducer 10a is used for reception, a satisfactory effect identical to the above case can also be achieved.

Referring to FIG. 6, when the plane transducer 10b is employed for transmitting plane waves in the direction shown by the arrow, ultrasonic waves are transmitted not only toward the point M, but are also emitted toward a variety of points including M1 and M2, before being reflected toward the concave surface transducer 10a. Based on this phenomenon, it is probable that the concave surface transducer 10a will receive not only component K from the point M, but will also receive components K1 and K2 of spherical or cylindrical waves reflected from points M1 and M2, and a variety of other points as well.

Referring now to FIGS. 7 and 8, the wave component K reflected toward the center of curvature of the concave surface of the concave-surface transducer 10a is effectively converted into electric signals by the concave surface transducer 10a. On the other hand, wave components K1 and K2 reflected by points M1 and M2 cannot effectively be converted into electric signals as a result of phasewise interference generated on the surface of the piezoelectric film 101a. Accordingly, even when the plane transducer 10b is employed for transmission and the concave-surface transducer 10a is employed reception of ultrasonic waves, a satisfactory conversion effect can also be achieved, which is substantially equivalent to the case, described above, of using the concave surface transducer 10a for transmission and the plane transducer 10b for reception of ultrasonic waves.

Figure 9:
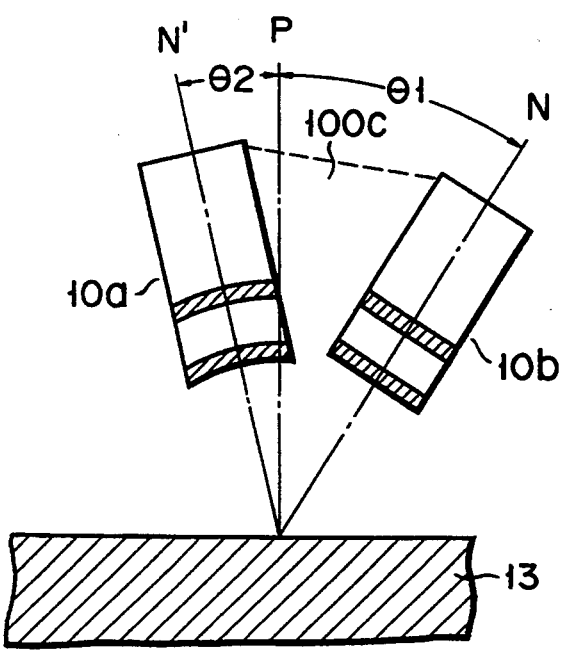

As shown in FIG. 9, the ultrasonic sensor 91 can precisely be adjusted to the desired angle of incidence merely by properly adjusting an angle $\theta_1$ between a point N orthogonally intersecting the transmission/reception surface of the plane transducer 10b and a point P orthogonally intersecting the surface of the sample 13.

In addition, an optical microscope 33 (FIG. 1) for optically observing the sample 13 and a photographic unit 34 for executing microscopic photography are respectively secured to the horizontal frame 32. Since the optical microscope 33 and the photographic unit 34 are well known and not always necessary for the ultrasonic micro spectrometer embodied by the invention, no description is given here.

Figure 10:
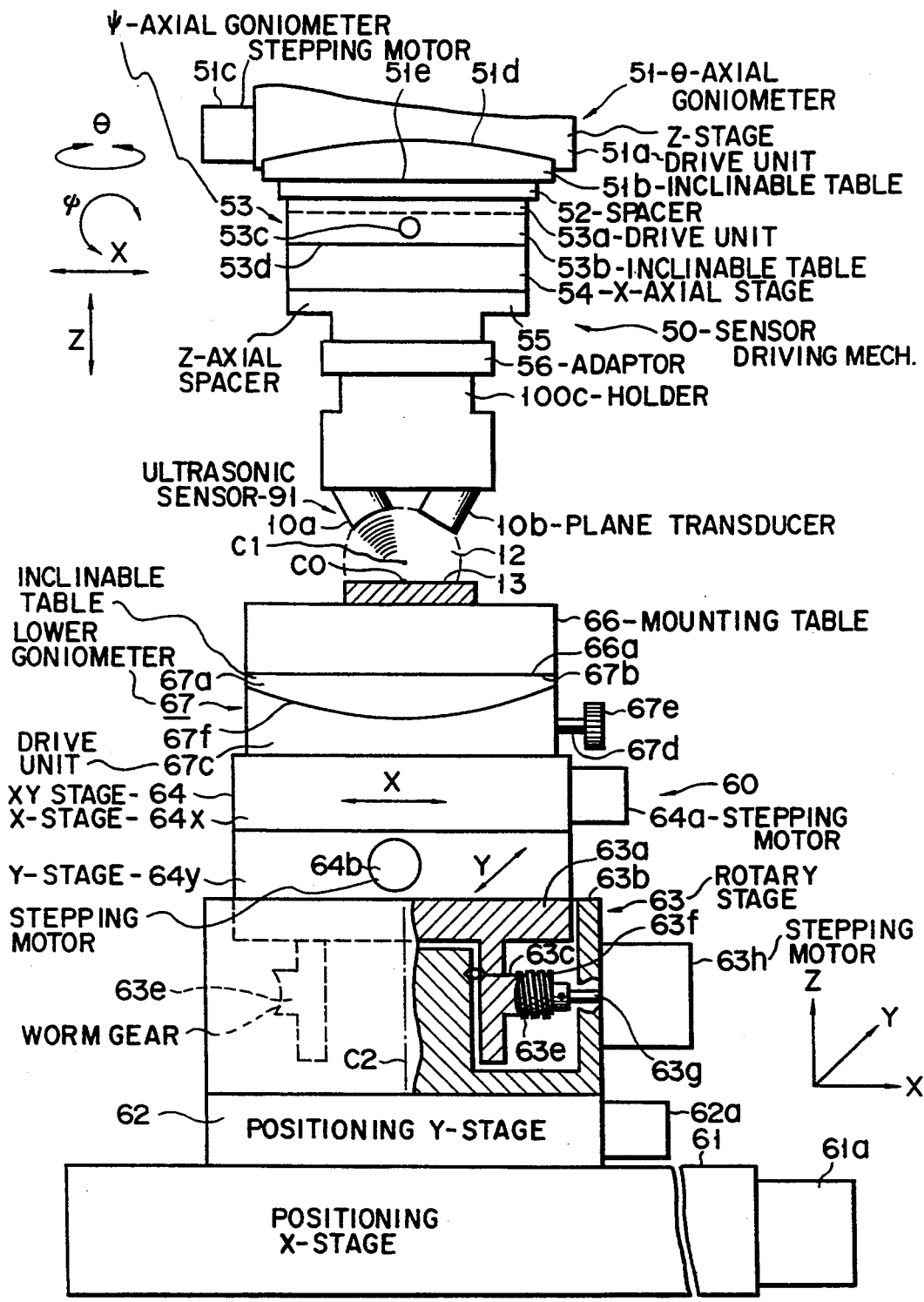
FIG. 10 illustrates an enlarged lateral view of the sensor mechanism and multiple stage shown in FIG. 1.

The multiple-stage sensor driving mechanism 50 as shown in FIGS. 1 and 10, is secured directly below the z-stage 50a. The multiple-stage sensor driving mechanism 50 is composed of a plurality of stacked instruments including the following: a Θ-axial goniometer 51 which is installed on the top of the stacked assembly and employed for establishing the angle of incidence; a spacer 52 from which the sensor driving mechanism 50 is supported; a Ψ-axial goniometer 53 which finely adjusts the tilt angle of the ultrasonic sensor 91 in a direction traverse to the direction of inclination of the Θ-axial goniometer 51; an x-axial stage 54 which is employed for correcting the focal position of the ultrasonic sensor 91 in the x-axial direction; and a z-axial spacer 55 which is employed for correcting the focal position of the ultrasonic sensor 91 in the z-axial direction. A holder 100c is secured via an adaptor 56 to the z-axial spacer 55 and is installed at the bottom of the stacked assembly of the sensor driving mechanism 50. The adaptor 56 is engageable with and disengageable from the holder 100c via a screw means, for example.

The Θ-axial goniometer 51 inclines the ultrasonic sensor 91 in the direction of the Θ axis in order to establish the angle of incidence. To accomplish this function, goniometer 51 is provided with a drive unit 51a and an inclinable table 51b. The Θ-axial goniometer 51 is preferably driven by a stepping motor 51c. Since the internal structure of the drive unit 51a is conventionally known, it is not shown here. When rotating the stepping motor 51c connected to the main shaft (not shown) of the Θ-axial goniometer 51, a worm gear (not shown) coupled to the main shaft is engaged with a worm wheel (not shown) which is installed along a curved surface 51d of the inclinable table 51b to incline the table 51b in the direction of the Θ axis through the plurality of components secured to the horizontal surface 51e directly beneath the inclinable table 51b, and finally the ultrasonic sensor 91 is stopped upon arrival at the optimal angle of incidence compatible with a selected measuring operation.

When establishing the optimal angle of incidence by driving the Θ-axial goniometer 51, it is desirable that the ultrasonic waves reflected from the surface of the sample 13 be effectively received by the ultrasonic sensor 91. More specifically, it is desirable that the plane formed between the surface of the sample 13 and the ultrasonic sensor 91 by the incident waves and the reflective waves be formed vertical to the surface of the sample 13. To satisfy this requirement, the ultrasonic micro spectrometer according to the invention also includes a Ψ-axial goniometer 53 secured to the bottom horizontal surface 51e of the inclinable table 51d of the Θ-axial goniometer 51 via the spacer 52. The Ψ-axial goniometer 53 inclines the ultrasonic sensor 91 in the direction of an axis Ψ. The Ψ-axial goniometer 53 is provided with a drive unit 53a and an inclinable table 53b identical to the drive unit 51a and the inclinable table 51b provided for the Θ-axial goniometer 51. In addition, the main shaft (not shown) inside of the drive unit 53a may be manually driven by means of a knob 53c coupled with the main shaft. When the operator manually operates the knob 53c, the ultrasonic sensor 91 is inclined in the direction of the Ψ axis through the components secured between the bottom horizontal surface 53*d* of the inclinable table 53*b* and the ultrasonic sensor 91, before eventually being held at an optimal angle of incidence.

Furthermore, when inclining the ultrasonic sensor 91 by operating the θ-axial goniometer 51, it is desirable that the focus of the ultrasonic sensor 91 be exactly positioned on the center axial line (in the direction vertical to the surface of the sample 13) and at the point of inclination CO of the θ-axial goniometer 51. The point of inclination CO refers to the point about which the θ-axial goniometer 51 inclines the sensor 91 with respect to the surface of the sample 13, as shown in FIG. 10. This permits the focus to be held at a constant position against the sample 13 independent of the variation of the angle of incidence. To achieve this, the ultrasonic micro spectrometer embodied by the invention includes an X-axial stage 54 and a Z-axial spacer 55 disposed directly beneath the Ψ-axial goniometer 53. The X-axial stage 54 corrects the focal position of the ultrasonic sensor 91 in the direction of the X axis. More specifically, the X-axial stage is slidably disposed on the plane surface 53*d* directly below the inclinable table 53*b* of the Ψ-axial goniometer 53, so as to be slidable in the direction of the X axis by any conventional means. In addition, the focal position of the ultrasonic sensor 91 can properly be adjusted in the X-axial direction by manually sliding the X-axial stage 54.

The Z-axial spacer 55 is secured to the X-axial stage 54 and brings the Z-axial-directional focus of the ultrasonic sensor 91 into accord with the point of inclination CO of the Θ-axial goniometer 51. The Z-axial spacer 55 may be elongated and contracted in the direction of the Z axis when the operator manually operates the knob 53*c*. By finely adjusting the X-axial stage 54 and the Z-axial spacer 55, the focal position of the ultrasonic sensor 91 is brought into perfect accord with the point of inclination CO of the Θ-axial goniometer 51.

As shown in FIGS. 1 and 10, a multiple-stage table 60 is mounted on the base 20 of the ultrasonic micro spectrometer. The multiple-stage table 60 is composed of a plurality of stacked instruments including the following: a positioning X-stage 61 placed on the base 20, a positioning Y-stage 62, a rotary stage 63, an XY-stage 64, and a dual goniometer 65, respectively.

It is desirable that the upper surface of the sample 13 mounted on the upper surface of the multiple-stage table 60 be maintained level with the XY drive surface of the multiple-stage table 60. To achieve this, a dual goniometer 65 is provided for the multiple-stage table 70. The dual goniometer 65 is composed of an upper sample mounting table 66 and a lower goniometer 67. More specifically, in order that the sample mounting table 66 can be moved in conjunction with the inclinable table 67*a* of the goniometer 67, the plane surface 66*a* at the bottom of the sample mounting table 66 is secured to the upper plane surface 67*b* of the inclinable table 67*a*.

When the operator manually rotates a knob 67*e* connected to the main shaft 67*d* of the drive unit 67*c* of the goniometer 67, a worm gear (not shown) disposed on the main shaft 67*d* inside of the drive unit 67*c* is engaged with a worm wheel (not shown) which is provided along the curved lower surface 67*f* of the inclinable table 67*a*, whereby the worm wheel is rotated to incline the table 67. As a result, the sample mounting table 66 is also inclined. In other words, by properly rotating the knob 67*e*, the upper surface of the sample 13 can be kept level with the XY drive surface of the multiple-stage table 60.

The XY-stage 64 disposed below the dual goniometer 65 moves the sample 13 in the X and Y directions so that the surface of the sample 13 can be scanned in both X and Y directions by the ultrasonic sensor 91. The XY-stage 64 is composed of an x-stage 64*x* which moves the sample 13 in the direction of x axis and a y-stage 64*y* which moves the sample 13 in the direction of y axis. The x and y stages 64*x* and 64*y* are respectively displaced by any conventional system, and preferably by stepping motors 64*a* and 64*b*.

In order to enable the ultrasonic micro spectrometer to properly deal with a variety of measuring requirements, it is desirable that the measuring system be provided with a specific mechanism capable of rotating either the sample-mounting table 66 or the ultrasonic sensor 91 relative to each other in a plane parallel to the XY-drive surface of the multiple-stage table 60. To achieve this, the ultrasonic micro spectrometer embodied by the invention is provided with a rotary stage 63 disposed directly below the XY stage 64. The rotary stage 63 includes a circular turntable 63*a* capable of being rotated around a center axial line C2. The circular turntable 63*a* is supported by a supporting member 63*b* via a supporting roller 63*c*. A worm gear 63*e* is provided on the circumferential surface of a downward projection 63*d* below the circular turn table 63*a*. A main shaft 63*g* is provided on which a worm wheel 63*f* is mounted, and the worm wheel 63*f* is engaged with the worm gear 63*e* and is rotated by a stepping motor 63*h*. Therefore, the circular turntable 63*a* may be rotated by the rotation of the worm wheel 63*f*. The circular turntable 63*a* is capable of turning a full 360°. While the rotary stage 63 is rotated with the stepping motor 63*h*, and simultaneous with the delivery of an optional number of pulses from the controller 17 to the stepping motor 63*h*, the controller 17 also instructs the digital oscilloscope 18*a* to initiate the introduction of electric signals.

The ultrasonic micro spectrometer according to the present invention performs measuring and evaluation processes with respect to a specific minimal region of the sample 13 by varying the angle of incidence. However, independent of the variation of the angle of incidence, it is essential for the system to ensure that the minimal region constantly coincides with the focus of the ultrasonic sensor 91. In other words, it is essential for the system to ensure that the center axial line C2 of the circular turntable 63*a* perfectly coincides with the focal point C1 of the ultrasonic sensor 91. To achieve this, the ultrasonic micro spectrometer embodied by the invention is provided with a positioning Y-stage 62 and another positioning x-stage 61 to displace the rotary stage 63 in the direction of the Y and X axes. The positioning Y-stage 62 is slidably moved in the direction of the Y axis above the positioning X-stage 61 by a conventional means, preferably, by a stepping motor 62*a*.

The positioning X-stage 61 disposed below the positioning Y-stage 62 not only positions the turntable 63*a*, but also is capable of displacing the sample 13 to a position below the optical microscope 33. The positioning X-stage 61 is slidably moved in the direction of the X axis by a stepping motor 61*a*.

The ultrasonic micro spectrometer according to the present invention includes a scanning means composed of the XY-stage 64 for directly displacing the sample 13. However, scanning movement may also be provided on the side of the ultrasonic sensor 91 and/or with the assistance ultrasonic sensor 91. For example, if the sample 13 has a large size, or in the event that the liquid coupler 12 cannot properly be mounted on the surface of the sample 13, then it is necessary to mount a water container, filled with the liquid coupler 12, on the sample mounting table 66, and place the sample 13 inside the water container. In this case, if the scanning XY-stage 64 on the side of the sample 13 were driven quickly, then the liquid coupler 12 would possibly slosh out of the water container. To prevent this, in the case of a sample that cannot easily be mounted with the liquid coupler disposed on the sample, or in the case of a large sample, then the ultrasonic sensor 91 may be disposed such that the sensor itself performs the scanning operations in the directions of the X and Y axes. Furthermore, scanning operations may be performed in the X and Y directions by displacing the ultrasonic sensor 91 at a fast speed in one of the X or Y directions, while simultaneously displacing the sample 13 slowly in the other direction. In this case, the scanning movement on the part of the ultrasonic sensor 91 may be provided at a fast speed by applying a "voise" coil motor, for example. Furthermore, in order to provide scanning movement on the part of the ultrasonic sensor 91, it is essential for the USMS system to install such a scanning means above the Θ-axial goniometer 51.

The ultrasonic micro spectrometer according to the present invention is provided with a rotary stage 63 on the side of the sample 13 so that the sample can be rotated. However, instead of this arrangement, a means for rotating the ultrasonic sensor 91 may also be provided. In this case, in order that the center axis $C_o$ of the rotating means accurately coincides with the focal point C1, it is essential for the USMS system to provide such a rotating means above the Θ-axial goniometer 51, or at a position higher than the scanning unit provided on the side of the ultrasonic sensor 91.

In order to precisely adjust the focal depth of the ultrasonic sensor 91, the USMS system may provide a Z-stage 50a (FIG. 1) driven in the direction of the z axis vertical to the XY drive surface on the side of the ultrasonic sensor 91. When installing the Z-stage 50a on the side of the ultrasonic sensor 91, it is essential that the Z-stage 50a be disposed above the Θ-axial goniometer 51. This is because in order to vary the distance between the sample 13 and the ultrasonic sensor 91 and to bring the focus of the sensor into perfect coincidence with the point of inclination CO, the sensor driving mechanism 50 must be completely displaced as a whole.

Figure 11:
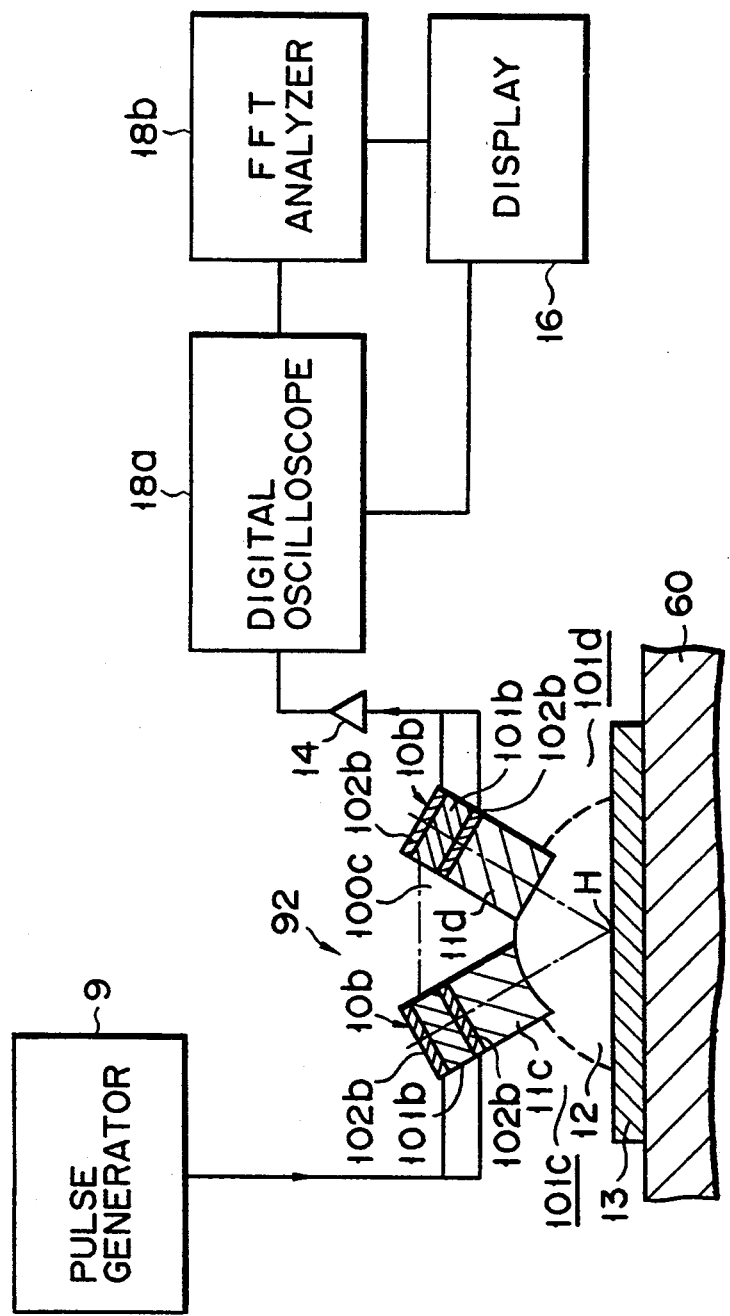
FIG. 11 schematically illustrates another block diagram of an ultrasonic micro spectrometer according to the second embodiment of the invention.

FIG. 11 schematically illustrates a block diagram of the ultrasonic micro spectrometer according to the second embodiment of the invention. The first and second embodiments of the invention differ respectively due to the structure of the ultrasonic sensor 92. Accordingly, the following description refers solely to the ultrasonic sensor 92.

The ultrasonic sensor 92 is provided with a concave surface transducer 101c and a plane transducer 101d. The concave surface transducer 101c consists of the following: A transmission/reception assembly unit 10b composed of a plane piezoelectric film 101b and a pair of plane electrodes 102b sandwiching the plane piezoelectric film 101b therebetween; and a delay element 11c having a concave transmission/reception surface at the tip thereof, wherein the delay element 11c is bonded to the transmission/reception assembly unit 10b to complete the formation of the plane transducer 101d. On the other hand, a plane transducer 101d consists of a transmission/reception assembly unit 10b and a delay element 11d having a plane transmission/reception surface on the tip thereof, wherein the delay element 11d is bonded to the transmission/reception assembly unit 10b to complete the formation of the plane transducer 101d. The concave surface transducer 101c and the plane transducer 101d are respectively manufactured by sequentially laminating a gold film 102b, a zinc oxide film 101b, and another gold film 102b on the delay element 11c or 11d by applying either vacuum evaporation or a sputtering process. The delay element 11c or 11d may be fabricated from melted quartz, for example.

The concave surface transducer 101c and the plane transducer 101d are respectively held by a holder memmber 100c.

Except for the two differences mentioned below, the ultrasonic sensor 92 according to the second embodiment of the invention functions identically to the ultrasonic sensor 91 described previously. First, the ultrasonic sensor 92 differs from the sensor 91 in that the sensor 92 generates convergent ultrasonic waves which converge dependent on the difference between the velocity of sound in the delay element and the velocity of sound in the transmission liquid 12. Secondly, the focus of the ultrasonic sensor 92 deviates slightly in a direction away from the delay element 11c and against the center of curvature of the concave surface of the delay element 11c.

As with the ultrasonic sensor 91 according to the first embodiment, the ultrasonic sensor 92 precisely measures physical characteristics, in particular elastic characteristics, within a minimal region of the sample independently of the orientation of the transmission/reception surface of the concave surface transducer 101c of the ultrasonic sensor 92.

Figure 12:
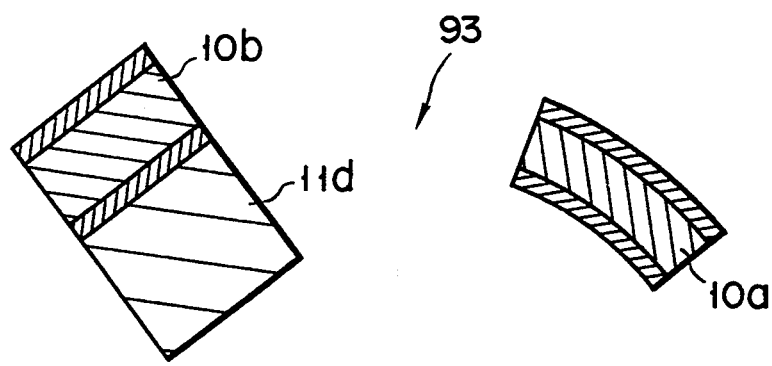
FIGS. 12 and 13 respectively illustrate sectional views of an ultrasonic sensor according to the third embodiment of the invention.
Figure 13:
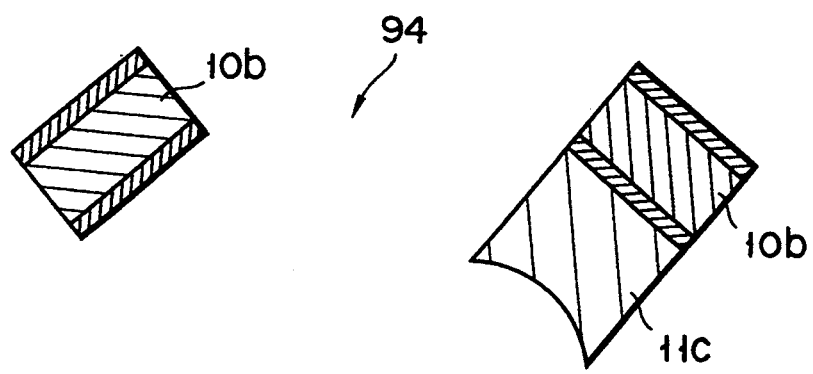

FIGS. 12 and 13 respectively illustrate the structure of the ultrasonic sensors employed in the ultrasonic micro spectrometer according to the third embodiment of the invention. The ultrasonic sensors 93 and 94 according to the third embodiment of the invention are respectively composed of a concave surface transducer and a plane transducer, wherein either of these ultrasonic sensors may be provided with a delay element 11c or 11d. The other transducer has a structure identical to that of the ultrasonic sensor 91 according to the first embodiment.

Figure 14:
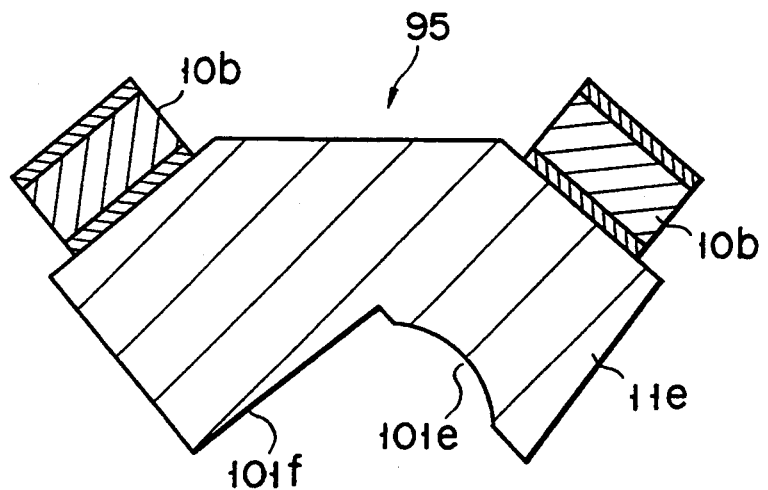
FIG. 14 illustrates a sectional view of an ultrasonic sensor according to the fourth embodiment of the invention.

FIG. 14 illustrates the structure of an ultrasonic sensor 95 employed in the ultrasonic micro spectrometer according to the fourth embodiment of the invention. The ultrasonic sensor 95 according to the fourth embodiment comprises a delay element 11e having an integrally combined concave surface 101e and a plane surface 101f. Although the delay element is made from the same material as that of the preceding delay elements 11c and 11d, the delay element 11e is provided with both recessed and plane transmission/reception surfaces. It is further evident that the ultrasonic sensors according to the third and fourth embodiments of the invention are capable of achieving results comparable to those which are achieved by the preceding ultrasonic sensors according to the first and second embodiments.

The longitudinal width L of the plane transducers according to the first through fifth embodiments should be selected so as to satisfy the following expression (1), shown below:

$$L \geq (1/\sin \beta) \cdot (Vw/\omega) \tag{1}$$

where Vw designates the velocity of sound in the liquid coupler, $\omega$ designates either the time-base frequency of an ultrasonic wave transmitted from the ultrasonic sensor or the dip frequency based on the distribution of spectral intensity, and $\beta$ designates a value expressing the range of incident angles which may be selected for the ultrasonic sensor.

In relation to the first embodiment, a specific example shall be described below, in which the concave surface transducer 10a is employed for the transmission of ultrasonic waves, and wherein the plane transducer is employed for reception of ultrasonic waves.

Figure 15:
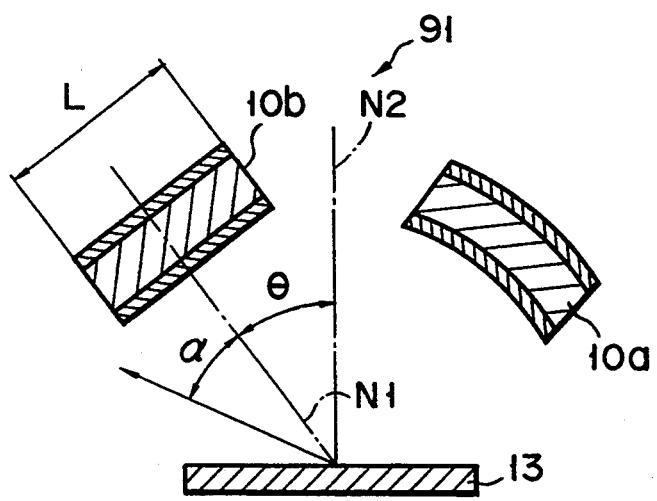
FIG. 15 illustrates a sectional view which explains the relationship between the width in the longitudinal direction of the plane transducer of the ultrasonic sensor and a component of the angle of incidence.
Figure 16:
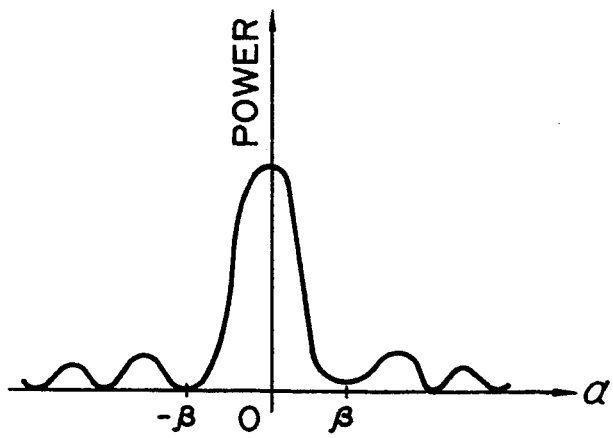
FIGS. 16 and 17 graphically designate output characteristics of the ultrasonic sensor in relation to the incident-angle component shown in FIG. 15.
Figure 18:
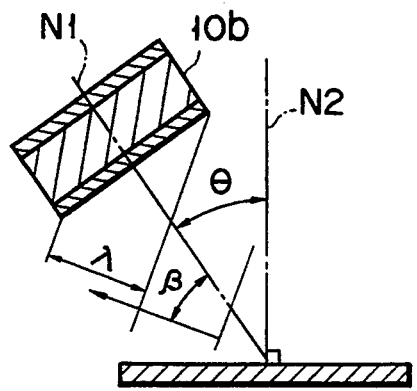
FIG. 18 illustrates a sectional view which explains the capability of the ultrasonic sensor shown in FIG. 15 for selecting the angle of incidence.
Figure 17:
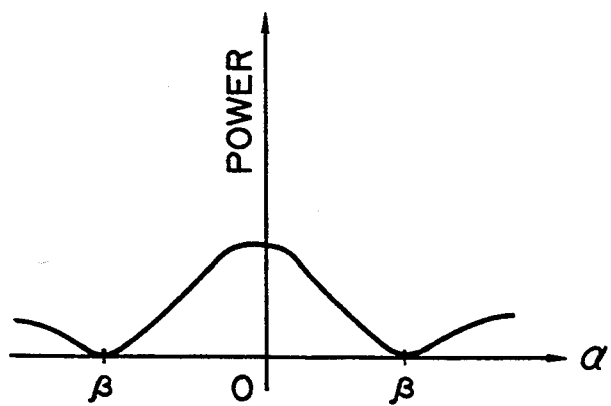

Referring to FIG. 15, the angle of incidence $\theta$ of the plane transducer 10b with respect to the surface of the sample 13 is defined between a normal line $N_1$ of the plane transducer 10b and a normal line $N_2$ on the surface of the sample 13. As shown in FIG. 15, assuming that the ultrasonic wave received by the plane transducer 10b contains wave components which deviate from the angle of incidence $\theta$ by an angle $\alpha$, in this case, it is known that the ultrasonic sensor 91 outputs signals corresponding to ultrasonic waves as shown in FIGS. 16 and 17. More specifically, in the case where $\alpha=0$, ultrasonic waves are vertically transmitted to the plane transducer 10b. If, however, the ultrasonic transducer 10b has a substantial width L, even if the angle $\alpha$ were narrow, the intensity of the ultrasonic waves output from the ultrasonic sensor declines sharply as the angle deviates from the incident angle $\theta$. Generally, the output intensity is reduced to zero when the angle $\alpha$ is equal to $\beta$. It is therefore clear from FIG. 18 that $\beta$ should satisfy the equation (2) shown below:

$$\beta = \sin^{-1}(\lambda/L) \quad (2)$$

where $\lambda$ designates the ultrasonic wavelength, and further where $\lambda = Vw/\omega$. As a result of the phasewise interference which takes place across the width of the plane transducer 10b, the ultrasonic wave components which are deviated from the incident angle $\theta$ by the angle $\beta$, according to equation (2), are reduced to zero. In other words, $\beta$ defines a parameter whereby the ultrasonic sensor 91 can output only those ultrasonic wave components having a substantial intensity falling within a range $\theta \pm \beta$. When $\beta$ is defined as described above, the range of incident angles available for the ultrasonic sensor are selected accordingly, and the width L for the plane transducer 10b incorporating such a incident angle range is computed based on the above equations (1) and (2).

The output characteristics of the ultrasonic sensor, as well as the above expressions (1) and (2), may be satisfied even in the case where a plane transducer is employed on the transmission side of the ultrasonic sensor. Further, similar performance is achieved whether or not delay elements are employed in either or both of the ultrasonic transducers.

Specific examples of the operation of the ultrasonic micro spectrometer according to the present invention shall be described below.

Preparation for a Measuring Operation

Initially, an operator mounts the sample 13 on the upper table 66 of the multiple-stage table 60. When positioning the multiple-stage table 60 in the direction of the X-axis, the X-stage 64x is displaced through operation of the stepping motor 64a. Similarly, when positioning the multiple-stage table 60 in the direction of the Y-axis, the Y-stage 64y is displaced through operation of the stepping motor 64b. In order to set a desired angle of incidence, the inclinable table 51b of the $\Theta$-axial goniometer 51 is tilted through operation of the stepping motor 51c.

Measurement of the Phase Velocity of Elastic Surface Waves

Figure 19:
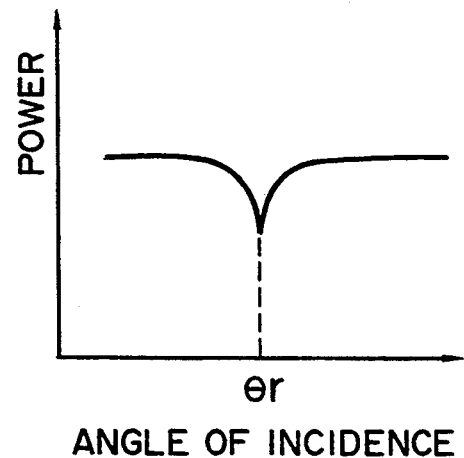
FIGS. 19 through 23 respectively graphically designate the functional performance of the ultrasonic micro spectrometer according to the invention; wherein FIGS. 19 and 20 graphically designate the relationship between the angle of incidence and the intensity of ultrasonic waves and the relationship between the angel of incidence and the phase characteristics.

In order to measure the phase velocity of an elastic surface wave, ordinarily a non-laminated sample is used. After completing the preparatory steps mentioned above, the pulse generator 9 is activated to feed a burst signal to the concave surface transducer 10a while the frequency of the burst signal is swept across a predetermined range. Ultrasonic waves transmitted to the sample by the concave surface transducer 10a are reflected on the surface of the sample 13, and the reflected waves are received by the plane surface transducer 10b, which converts the received waves into electric signals. As described above, the digital oscilloscope 18a is used for detecting time-base waveforms from the signals output from the ultrasonic sensor 92, and then the FFT analyzer 18B transforms the detected time-base waveforms into a Fourier series at a fast speed, with the result that both the distribution of spectral intensity and that of spectral phase are shown on the display screen 16. varying the angle of incidence, as to obtain the relationship between the intensity of the ultrasonic wave and the angle of incidence, as shown in FIG. 19. Based on thus obtained relationship, the control system precisely computes the angle of incidence $\theta r$ at which the intensity of the ultrasonic wave is minimized, as shown in FIG. 19.

Based on the computed angle of incidence $\theta r$, the control system then computes a phase velocity Vp of the elastic surface wave by applying the following equation (3), shown below:

$$Vp = Vw/\sin \theta r \quad (3)$$

wherein Vw designates the velocity of sound in the liquid coupler 12.

It is well known that the phase velocity Vp of an elastic surface wave provides an important parameter which quantitatively expresses the elastic property of the sample.

Figure 20:
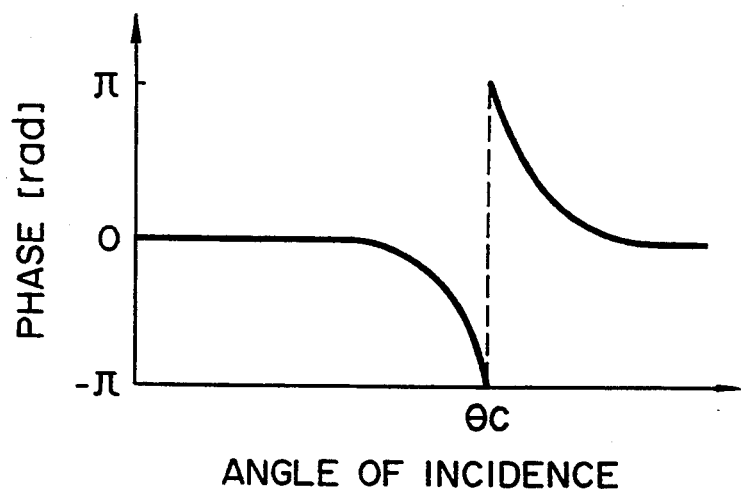

Furthermore, as described below, the phase velocity Vp of the elastic surface wave can also be computed by applying a distribution based on the spectral phase. Based on the distribution of the phase of the spectrum, data designating the relationship between phase and incident angle, as well as the relationship between phase and intensity of the ultrasonic waves, are respectively shown on the display screen 16. In this case, as shown in FIG. 20, the angle of incidence $\theta c$ at which either a rotation or a shift of phase occurs at a specific phase of an arbitrary frequency component, is determined by varying the angle of incidence. Generally, the angle of incidence $\theta c$ should coincide with the angle of incidence $\theta r$ discussed above and shown in FIG. 19. Thus, based on the angle of incidence $\theta c$, the control system can also compute the phase velocity Vp of the elastic surface wave based on the following equation (4), shown below:

$$Vp = Vw/\sin \theta c \quad (4)$$

Figure 21:
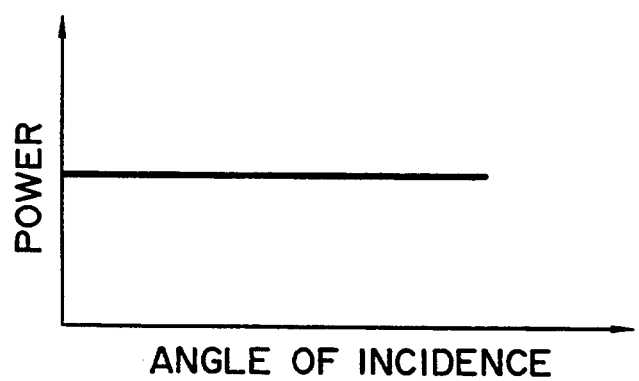

As may be seen by comparing FIG. 20 and FIG. 21, the phase continues to be variable at the angle $\theta c$ even if the relationship between the intensity of the ultrasonic wave and the angle of incidence is constant. In other words, the phase is variable even with a sample for which there is no specific angle of incidence $\theta r$, as shown in FIG. 19, at which the intensity of the ultrasonic wave becomes a minimum. Therefore, in contrast to the case of measuring only intensity of the ultrasonic wave, the ultrasonic micro spectrometer according to the present invention can effectively be used with a greater variety of specimens, by observing the distribution between the angle of incidence and the phase of the spectrum.

The ultrasonic micro spectrometer according to the present invention is capable of performing a variety of measurements on a sample based on the distribution of the phase of the spectrum in order to identify whether the sample is made from a non-laminated material or not, for example. This is because, if the angle of incidence $\theta c$ remain constant across all frequencies, then it can be determined that the sample does not contain a laminated structure formed from different layers. On the other hand, if the angle of incidence $\theta c$ varies at different frequencies, then the ultrasonic micro spectrometer can identify the sample as having a laminated structure. In the latter case, the ultrasonic micro spectrometer can also generate useful data expressing the elastic characteristics and strata structure of the sample in detail, by displaying various graphs on the display screen designating relationships between different frequencies and incident angles $\theta c$.

Measurement of the Distribution Curve for Elastic Surface Waves

Figure 22:
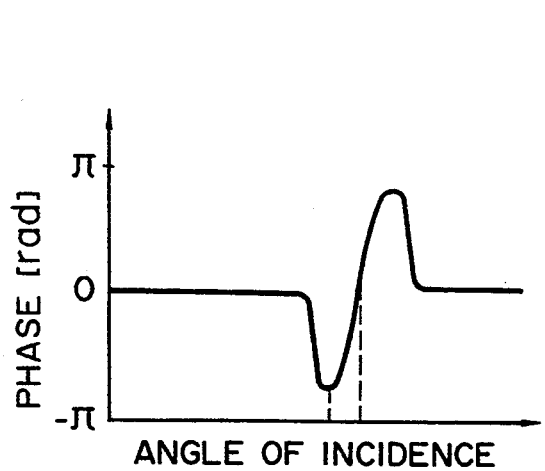
Figure 23:
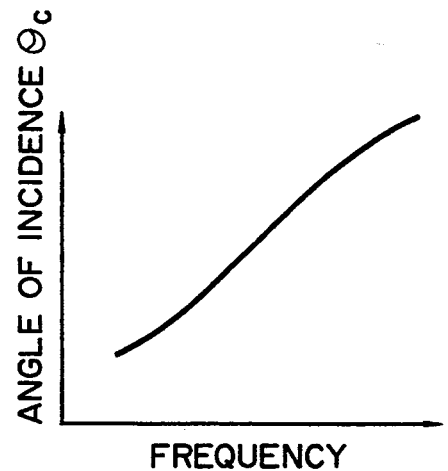

By way of a test example, the inventors measured the distribution curve of an elastic surface wave applied to a sample 13 comprising plated or coated film layers formed on a substrate. Processes identical to the measurements of the phase velocity of elastic surface waves, as described above, were performed at a variety of different frequencies. Finally, the ultrasonic micro spectrometer graphically displayed the relationship between ultrasonic frequencies and the angle of incidence at which the variation in phase was detected, as shown in FIGS. 22 and 23. Generally, this relationship is referred to as the "dispersion curve" and provides an important source of data for characterizing the elastic properties of the sample 13.

Measurement of Layer Thickness

In order to measure the thickness of laminated layers, the inventors used a sample 13 comprising plated or coated film layers formed on a substrate.

While measuring the thickness of the laminated layers of the sample 13 at a specific incident angle $\theta 1$, the reflective intensity of the ultrasonic waves was minimized, while simultaneously the specific frequency $f_c$ at which the phase of the ultrasonic waves started to vary was determined. In particular, the frequency component $f_c$ has a specific relationship to layer thickness "d" as shown below:

$$f_c \times d = c \quad (5)$$

where C designates a constant determined by the elastic characteristics of the substrate, the laminated layers, the liquid coupler, and the angle of incidence $\theta 1$ the ultrasonic waves.

By using a sample of the same type as the sample 13 but having a known layer thickness, the value of the constant C, shown above, can preliminarily be computed before actual measurement of the layer thickness of the sample, thereby calibrating the apparatus. Therefore, if the angle of incidence $\theta$ is held constant, then the layer thickness "d" of the sample can be computed by applying the above equation.

If a false "Sezawa" wave becomes excited as an elastic surface wave on a sample containing laminated film layers, then the energy of the surface wave also leaks in the direction of the depth of the laminated sample, thus lowering the reflective intensity.

Measurement of Anisotropy

To measure anisotropy, an anisotropic sample such as a crystal or an elongated film is employed as the sample 13. The phase velocity of the elastic surface waves on the surface of the anisotropic sample is variable according to the direction of propagation of the elastic surface waves. More particularly, depending on the direction of propagation of the elastic surface waves, either the angle of incidence $\theta r$ at which the intensity of ultrasonic waves becomes a minimum, or the angle of incidence $\theta c$ at which a phase shift occurs, is subject to variation. This variation in turn signifies that either the symmetry of the crystal or the direction and extent of elongation of the film can be measured by detecting a variation of either the angle of incidence $\theta r$ or the angle of incidence $\theta c$.

While performing the preparatory processes before measurement of anisotropy, the positioning X-stage and the positioning Y-stage are respectively moved to precisely align the focal point C1 of the ultrasonic sensor with the center axial line C2 of the turntable 63a of the rotary stage 63. While maintaining this position, the USMS system detects the angle of incidence $\theta r$ by rotating the rotary table 63. Next, based on equations (3) and (4) cited earlier, the USMS system can measure the anisotropy of the phase velocity of elastic surface waves in the direction of propagation of the elastic surface waves on the sample 13.

There has been described above various specific examples for operating the USMS system of the present invention in order to perform a variety of measurement functions. In order to reliably perform the measurement processes described above, it is essential that the USMS system be capable of accurately detecting the angle of incidence $\theta$ of the ultrasonic waves which travel between the transmission/reception of the plane transducer and the surface of the sample.

Figure 24:
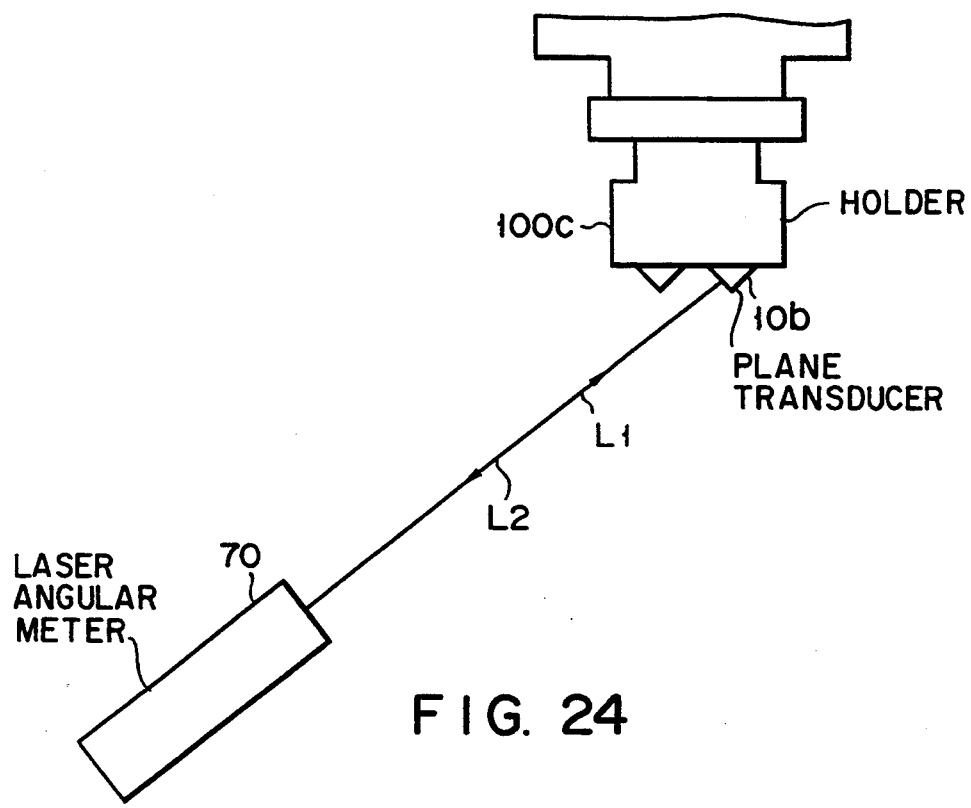
FIG. 24 schematically illustrates a mechanism for detecting the angle of incidence of the ultrasonic sensor employed in the ultrasonic micro spectrometer embodied by the invention.

FIG. 24 illustrates an example of the USMS system incorporating means for measuring the angle of incidence $\theta$. A laser angular meter 70 transmits a laser beam $L_1$ to the transmission/reception surface of the plane transducer 10b. The emitted laserbeam $L_1$ is then reflected by the transmission/reception surface of the plane transducer 10b, and the reflected laser beam $L_2$ is received by the laser angular meter 70 so that the angle of incidence $\theta$ can be detected. An optical element, for example a prism, may optionally be disposed in the light paths of the laser beams $L_1$ and/or $L_2$ for directing the laser beams.

When operating the USMS system incorporating the Z-axial stage 50a, the angle of incidence $\theta$ can be computed by applying the equation shown below:

$$\theta = \cos^{-1}(\Delta P(f)/Z) \times (V/4\pi f) \quad (6)$$

where Z designates the vertical distance between the ultrasonic sensor 91 and the surface of the sample 13, P(f) designates the phase at an optional frequency component "f", and V designates the velocity of sound in the liquid coupler 12. By expressing the above relationship between Z and P(f) as a linear graph, ΔP(f)/Z can be computed as the slope of the line defined by the above equation.

Figure 25:
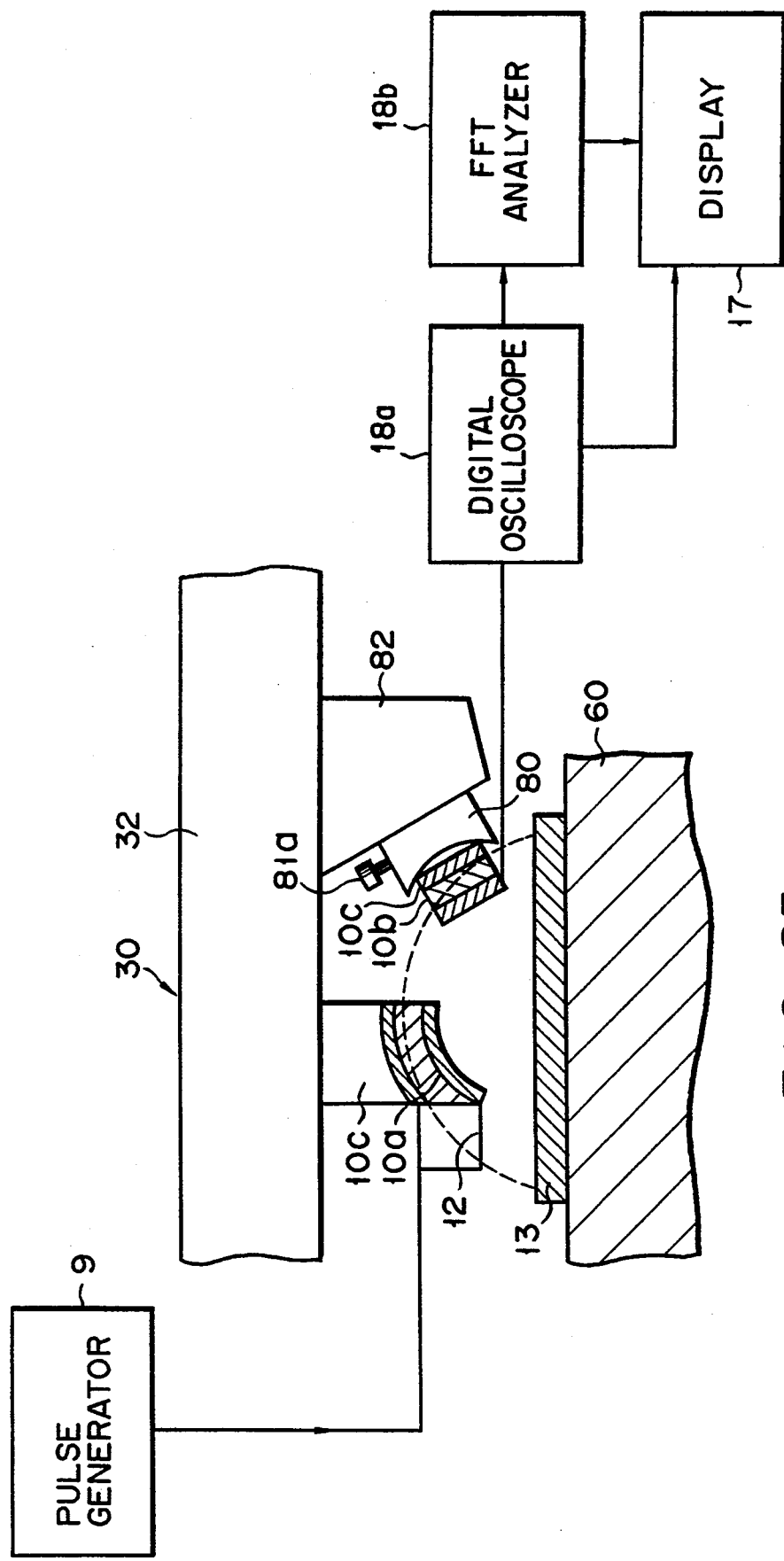
FIG. 25 schematically illustrates the essential components of an ultrasonic micro spectrometer according to the fifth embodiment of the invention.

FIG. 25 schematically illustrates a block diagram of the USMS system according to the fifth embodiment of the invention. According to this embodiment, the focus of the ultrasonic sensor is determined by the curvature of the concave surface of the concave surface transducer 10a, and the angle of inclination is determined by the degree of inclination of the plane transducer 10b. Therefore, although only the plane transducer 10b is inclined with respect to the sample, while the axis of the concave transducer 10a remains vertical as shown in FIG. 25, according to the fifth embodiment the USMS system can still properly control the angle of incidence of the ultrasonic sensor.

The transducer pairs thus far described in reference to FIGS. 2, 11, 12 and 13 can also be employed in the fifth embodiment. More specifically, as shown in FIG. 25, the ultrasonic sensor 91 comprises a concave surface transducer 10a and a plane transducer 10b. According to the fifth embodiment, the USMS system does not use the sensor driving mechanism 50, discussed earlier, but instead the concave surface transducer 10a is directly secured to a horizontal frame 32 of the frame body 30 (see FIG. 1) via the supporting member 10c. Accordingly, the height of the frame body 30 may be made lower than in the case of the preceding embodiments.

The supporting member 10c supporting the plane transducer 10b is secured to an the Θ-axial goniometer 80 having substantially the same internal structure as that of Θ-axial goniometer 51 employed in the sensor driving mechanism 50 of the preceding embodiments. The Θ-axial goniometer 80 is secured to the horizontal frame 32 via a supporting member 82. According to the fifth embodiment of the invention, various measuring operations can be precisely performed with respect to a specific target region of the sample 13 by setting the incident angle within a widely applicable range.

An example of a test performed by the inventors for measuring the critical angle θr for exciting a "Rayleigh" wave having a single degree of precision on the sample 13 using the USMS system of the fifth embodiment shall now be described.

While performing the test, the inventors used a sample 13 made from melted quartz, and water was used as the liquid, coupler 12. A concave surface transducer 10a having a cylindrical concave surface having a radius of 5 mm and a half angle aperture of 20 degrees was employed. In the course of the test, the pulse generator 9 was set to deliver a pulse signal having a frequency of 50 MHz to the concave surface transducer 10a.

Based on a velocity of sound in water of 1500 meters per second, and an ultrasonic frequency of $50 \times 10^6$ Hz, the width L of the plane transducer 10b was selected to be 17.2 mm according to the equation (1):

$$L = 1/\sin(0.1) \cdot (1500/50 \times 10^6) = 17.2 \text{ mm}$$

Figure 26:
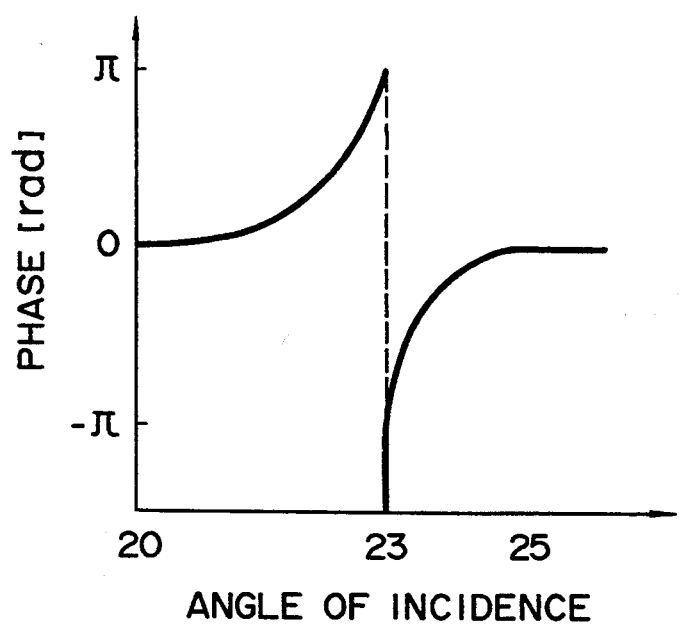
FIG. 26 graphically designates the relationship between angle of incidence and phase characteristics for determining the angle of incidence of an excited "Rayliegh" wave in melted quartz, wherein the graph shown in FIG. 26 demonstrates an actual example of the functional operation performed by the ultrasonic micro spectrometer shown in FIG. 25.

Based on the above conditions, the inventors measured the distribution of the phase spectrum of the reflected waves by manually operating the Θ-axial goniometer 51 and varying the angle of incidence of the plane transducer with respect to the sample in a range from 20 to 30 degrees. Finally, the above test revealed the results shown in FIG. 26. More specifically, as shown in FIG. 26, the phase of the reflective wave experienced a clear shift at an incident angle of $\theta = 23°$. Based on this data, the inventors were able to confirm that the critical angle θr for generating excitation of a "Rayleigh" wave in melted quartz occurred in the range from 23° to a maximum of 24°.

It should be apparent that the above described ultrasonic micro spectrometer possesses numerous advantages for enabling the measurement of a variety of samples, and that the invention therefore possesses important commercial and analytical utility. It should further be understood that the specific form of the invention hereinabove described is intended to be representative only, as certain modification within the scope of these teachings will become apparent to those of skill in the art.

Accordingly, reference shall be made to the following claims in determining the full scope of the invention.

What is claimed is:

1. An ultrasonic micro spectrometer for transmitting ultrasonic waves to the surface of a sample and receiving reflected ultrasonic waves from the surface of the sample, and analyzing frequencies of said reflected ultrasonic waves, comprising:

means for generating high-frequency electric signals;

an ultrasonic transducer assembly comprising first and second ultrasonic transducers each including a piezoelectric film disposed between a pair of electrodes, said first ultrasonic transducer having a concave surface for transmitting or receiving ultrasonic waves, and said second ultrasonic transducer including a planar surface for transmitting or receiving ultrasonic waves, wherein said high-frequency electric signals output from said high-frequency signal generating means are supplied to one of said first and second ultrasonic transducers, whereby a selected one of said first and second ultrasonic tranducers transmits ultrasonic waves to the surface of said sample, and an unselected one of said first and second ultrasonic transducers receives reflected ultrasonic waves reflected from the surface of said sample, and wherein said unselected one of said first and second ultrasonic transducers which receives ultrasonic waves reflected from the surface of said sample outputs electric signals corresponding to an intensity of the reflected ultrasonic waves;

a table for mounting said sample thereon;

scanning means for moving one of said ultrasonic transducer assembly and said table such that the table and said transducer assembly are moved relative to each other, for scanning a position of the transmitted ultrasonic waves across the surface of said sample in two directions, wherein said position of the transmitted ultrasonic waves on said sample relative to said one ultrasonic transducer is determined by the shape and position of said first ultrasonic transducer having a concave surface;

means for controlling an angle of incidence or reflective angle by tilting at least said second ultrasonic transducer having said planar surface with respect to said sample, wherein said angle of incidence or reflective angle is defined by an angle formed between a line normal to said planar surface of said second ultrasonic transducer and a line normal to the surface of said sample;

means for determining a distribution of spectral intensity based on the electric signals output from said unselected one of said first and second ultrasonic transducers which receives ultrasonic waves reflected from the surface of said sample, wherein said distribution of spectral intensity indicates an intensity of said reflective waves as a function of frequency; and means for determining a distribution of spectral phase, wherein said distribution of spectral phase indicates the phase of said reflected waves as a function of frequency.

2. An ultrasonic micro spectrometer according to claim 1, further comprising means for moving at least one of said ultrasonic transducer assembly and said table in a vertical direction for varying a vertical distance between said ultrasonic transducer assembly and said sample.

3. An ultrasonic micro spectrometer according to claim 1, wherein said first and second ultrasonic transducers are disposed in a holder maintaining a fixed angle between respective center lines of said first and second ultrasonic transducers, and wherein said means for controlling angle of incidence or reflective angle comprises means for moving said holder such that said first ultrasonic transducer and said second ultrasonic transducer are tilted in unison.

4. An ultrasonic micro spectrometer according to claim 3, wherein said means for moving said holder further comprises means for adjusting a focal position of said first ultrasonic transducer, said means for adjusting focal position comprising means for moving said ultrasonic transducer assembly in at least one direction for setting a focal position of said first ultrasonic transducer on a point of inclination of said ultrasonic transducer assembly.

5. An ultrasonic micro spectrometer according to claim 4, wherein said means for adjusting focal position further comprises means for vertically displacing said ultrasonic transducer assembly with respect to said sample such that a focus of said ultrasonic waves is incident on the surface of said sample while said focal position is held on said point of inclination of said ultrasonic transducer assembly.

6. An ultrasonic micro spectrometer according to claim 5, wherein said means for adjusting focal position further comprises means for moving said ultrasonic transducer assembly horizontally in two dimensions with respect to the surface of said sample.

7. An ultrasonic micro spectrometer according to claim 6, further comprising means for rotating at least one of said table and said ultrasonic transducer assembly.

8. An ultrasonic micro spectrometer according to claim 7, wherein said table has an axis of rotation and is rotatably mounted for rotation relative to said first ultrasonic transducer, and further comprising means for aligning said axis of rotation of said table with a focal position of said first ultrasonic transducer having said concave surface.

9. An ultrasonic micro spectrometer according to claim 8, further comprising a pulse motor for rotating said table about said axis of rotation, and a control means including means for generating pulses for driving said pulse motor, said control means sending instruction signals to said means for determining a distribution of spectral phase in order to initiate reception of electric signals output from said other ultrasonic transducer after generation of a predetermined number of pulses.

10. An ultrasonic micro spectrometer according to claim 1, wherein said first ultrasonic transducer comprises a curved piezoelectric film and a pair of curved electrodes.

11. An ultrasonic micro spectrometer according to claim 1, wherein said first ultrasonic transducer comprises a plane piezoelectric film and a pair of plane electrodes, and further comprising a delay element disposed on one of said plane electrodes, said delay element having a concave surface for transmitting or receiving ultrasonic waves.

12. An ultrasonic micro spectrometer according to claim 11, wherein said second ultrasonic transducer comprises a plane piezoelectric film and a pair of plane electrodes, and further comprising a delay element disposed on one of said plane electrodes, said delay element having a planar surface for transmitting or receiving ultrasonic waves.

13. An ultrasonic micro spectrometer according to claim 12, wherein said delay element of said first ultrasonic transducer and said delay element of said second ultrasonic transducer are formed together as an integral body.

14. An ultrasonic micro spectrometer according to claim 12, wherein a longitudinal width L of said plane piezoelectric film of said second ultrasonic transducer is determined by the following equation:

$$L \geq (1/\sin \beta) \cdot (Vw/\omega)$$

wherein Vw designates a velocity of sound in a liquid coupler disposed between said ultrasonic transducer assembly and said sample, wherein $\omega$ designates either a time-base frequency of ultrasonic waves transmitted from said one ultrasonic transducer or a dip frequency present in the distribution of spectral intensity, and wherein $\beta$ designates a value determining a range of incident angles which may be selected for the ultrasonic sensor such that components of waves reflected from the surface of said sample and received by said second ultrasonic transducer lie within said range $\theta \pm \beta$ where $\theta$ is an angle formed by a line normal to the planar surface of said second ultrasonic transducer and a line normal to the surface of said sample.

15. An ultrasonic micro spectrometer according to claim 1, wherein said first ultrasonic transducer comprises a spherical concave surface.

16. An ultrasonic micro spectrometer according to claim 1, wherein said first ultrasonic transducer comprises a cylindrical concave surface.

17. An ultrasonic micro spectrometer according to claim 1, wherein said high-frequency signals generated by said high-frequency signal generating means comprise burst signals swept across a predetermined frequency range.

18. An ultrasonic micro spectrometer according to claim 1, wherein said high-frequency signals generated by said high-frequency signal generating means comprise wide band pulse signals.

19. An ultrasonic micro spectrometer according to claim 1, further comprising means for measuring said angle of incidence or reflective angle by detecting a reflected laser beam reflected from the planar surface of said second ultrasonic transducer.

* * * * *